United States Patent
Lee et al.

(10) Patent No.: US 10,276,036 B2
(45) Date of Patent: Apr. 30, 2019

(54) ELECTRONIC SYSTEM AND CONTROL METHOD FOR THE SAME

(71) Applicants: Beijing Lenovo Software Ltd., Beijing (CN); Lenovo (Beijing) Co., Ltd., Beijing (CN)

(72) Inventors: Sang-ho Lee, Beijing (CN); Xiaotian Zhu, Beijing (CN)

(73) Assignees: Beijing Lenovo Software Ltd., Beijing (CN); Lenovo (Beijing) Co., Ltd., Beijing (CN)

( * ) Notice: Subject to any disclaimer, the term of this patent is extended or adjusted under 35 U.S.C. 154(b) by 0 days.

(21) Appl. No.: 14/868,766

(22) Filed: Sep. 29, 2015

(65) Prior Publication Data

US 2017/0004702 A1 Jan. 5, 2017

(30) Foreign Application Priority Data

Jun. 30, 2015 (CN) .......................... 2015 1 0374597

(51) Int. Cl.
*A63B 24/00* (2006.01)
*H04M 1/725* (2006.01)
(Continued)

(52) U.S. Cl.
CPC .............. *G08C 17/02* (2013.01); *A61B 5/112* (2013.01); *A61B 5/1116* (2013.01);
(Continued)

(58) Field of Classification Search
CPC .... G07C 5/008; G07C 5/0808; G07C 5/0858; G07C 5/0891; G07C 5/085; G07C 5/0866;
(Continued)

(56) References Cited

U.S. PATENT DOCUMENTS

2005/0192723 A1\* 9/2005 Noguchi ................ G07C 5/085
701/33.4
2006/0121958 A1 6/2006 Jung et al.
(Continued)

FOREIGN PATENT DOCUMENTS

CN 103399483 A 11/2013
CN 104095615 A 10/2014
(Continued)

OTHER PUBLICATIONS

First Chinese Office Action regarding Application No. 201510374597.0 dated Oct. 19, 2017. English summary provided by Unitalen Attorneys at Law.

*Primary Examiner* — Dionne Pendleton
(74) *Attorney, Agent, or Firm* — Harness, Dickey & Pierce, P.L.C.

(57) ABSTRACT

Provided is an electronic system and a control method for the electronic system. The electronic system includes a maintenance apparatus configured to maintain a position of the electronic system relative to a user in a case that the electronic system is worn by the user; a first acquisition apparatus configured to detect triggering data; and a processing apparatus configured to determine whether the triggering data meets a first condition, and control the electronic system to perform a preset function based on a result of the determination. When using a wearable electronic device including the electronic system, a user can control the electronic system to perform a preset function only by triggering the first acquisition apparatus, thereby simplifying the control operation. And the control method can be used for driving the electronic system to perform a preset function, thereby providing convenience in use.

5 Claims, 4 Drawing Sheets

(51) Int. Cl.
*H04Q 9/00* (2006.01)
*G08C 17/02* (2006.01)
*G06F 1/16* (2006.01)
*A61B 5/11* (2006.01)
*A61B 5/00* (2006.01)
*G06K 9/00* (2006.01)

(52) U.S. Cl.
CPC .......... *A61B 5/1123* (2013.01); *A61B 5/6807* (2013.01); *G06F 1/163* (2013.01); *G06K 9/00342* (2013.01); *G08C 2201/93* (2013.01)

(58) Field of Classification Search
CPC .......... G07C 1/22; G07C 1/24; G07C 5/0816; G04F 10/00; G04G 17/04; G04G 17/08; G04G 21/02; G04G 21/025; G04G 21/04; H04N 2005/4428; H04N 2005/4435; H04N 5/4403; G06F 1/163; G06F 2200/1637; G06F 3/011; G06F 3/017; G06F 19/3418; G06F 3/015; G06F 3/0312; G08C 17/02; G08C 19/28; G08C 2201/32; G08C 2201/93; A63B 24/00; A63B 24/0062; A63B 71/06; A61B 2560/0431; A61B 5/0006; A61B 5/04015; A61B 5/0478; A61B 5/048; A61B 5/0484; A61B 5/165; A61B 5/4839; A61B 5/6803; A61B 5/6816; A61B 5/6831; B60K 2350/1016; B60K 2350/1024; B60K 2350/1028; B60K 35/00; B60K 37/06; B60W 50/08; G05G 1/105; G06Q 30/0277; G16H 10/60
See application file for complete search history.

(56) References Cited

U.S. PATENT DOCUMENTS

| | | | |
|---|---|---|---|
| 2010/0117579 A1* | 5/2010 | Culbert | G06F 1/20 318/471 |
| 2011/0060215 A1* | 3/2011 | Tupin, Jr. | A61B 5/0507 600/425 |
| 2012/0274508 A1* | 11/2012 | Brown | G04F 10/00 342/357.25 |
| 2013/0041617 A1* | 2/2013 | Pease | A43B 3/0005 702/139 |
| 2015/0378330 A1 | 12/2015 | Xi et al. | |
| 2016/0227150 A1* | 8/2016 | Sun | G06F 3/011 |
| 2018/0280760 A1* | 10/2018 | Winsper | A63B 24/0062 |

FOREIGN PATENT DOCUMENTS

| | | |
|---|---|---|
| CN | 104267811 A | 1/2015 |
| CN | 104317394 A | 1/2015 |

* cited by examiner

ELECTRONIC SYSTEM AND CONTROL METHOD FOR THE SAME

CROSS REFERENCE OF RELATED APPLICATION

This application claims the priority to Chinese Patent Application No. 201510374597.0, entitled "ELECTRONIC SYSTEM AND CONTROL METHOD FOR THE SAME", filed with the Chinese State Intellectual Property Office on Jun. 30, 2015, which is incorporated by reference in its entirety herein.

FIELD

The present disclosure relates to the field of smart wearable electronic devices, and in particular to an electronic system and a control method for the electronic system applied in a wearable electronic device.

BACKGROUND

With increasing development of science and technology, various wearable electronic devices are more and more widely applied in and offer a great convenience to people's daily lives.

Generally, a conventional wearable electronic device (such as a smart bracelet and smart running shoes) needs to be used with a mobile terminal (such as a mobile phone) via which the wearable electronic device is triggered to perform a preset function. Taking smart running shoes as an example, a user wearing the smart running shoes needs to start a recording function of the smart running shoes via a mobile phone if the user wants to record running data.

As can be seen, the conventional wearable electronic device needs to be used with the mobile terminal via which the wearable electronic device is controlled to perform the preset function, and hence the control operation is complex.

SUMMARY

In order to address the above issue, the present disclosure provides an electronic system and a control method for the electronic system applied in a wearable electronic device, for simplifying a control operation of the wearable electronic device.

In order to achieve the above object, the present disclosure provides the following technical solutions.

The present disclosure provides an electronic system, which includes:

a maintenance apparatus configured to maintain a position of the electronic system relative to a user in a case that the electronic system is worn by the user;

a first acquisition apparatus configured to detect triggering data; and a processing apparatus configured to determine whether the triggering data meets a first condition, and control the electronic system to perform a preset function based on a result of the determination.

Preferably, in the above electronic system, the processing apparatus may generate a control instruction for controlling the electronic system to switch from a first mode to a second mode in a case that the triggering data meets the first condition.

Preferably, the above electronic system may further include a second acquisition apparatus operable in a data acquisition mode and a non-data acquisition mode, where the processing apparatus may be configured to control the second acquisition apparatus to switch from the data acquisition mode to the non-data acquisition mode or from the non-data acquisition mode to the data acquisition mode in a case that the triggering data meets the first condition.

Preferably, the above electronic system may further include a first communication apparatus, where the processing apparatus may be configured to send a control instruction to a first electronic device via the first communication apparatus for controlling the first electronic device to switch from a first mode to a second mode in a case that the triggering data meets the first condition.

Preferably, in the above electronic system, the first acquisition apparatus may be a spatial parameter acquisition apparatus or a pressure acquisition apparatus.

Preferably, in the above electronic system, the first acquisition apparatus may be operable in a trigger detecting mode and a data recording mode; and the processing apparatus may be configured to control the first acquisition apparatus to switch from the trigger detecting mode to the data recording mode or from the data recording mode to the trigger detecting mode in a case that the triggering data meets the first condition.

Preferably, the above electronic system may include a first body and a second body, where the maintenance apparatus may include a first maintenance apparatus arranged in the first body and configured to maintain a position of the first body on a first part of a user body, and a second maintenance apparatus arranged in the second body and configured to maintain a position of the second body on a second part of the user body; and the processing apparatus may be arranged in the first body.

Preferably, in the above electronic system, the first maintenance apparatus may include a first chamber having an opening, and the second maintenance apparatus may include a second chamber having an opening; and a position of the first body relative to the user body may be maintained by the first maintenance apparatus once the first part of the user body enters the first chamber, and a position of the second body relative to the user body may be maintained by the second maintenance apparatus once the second part of the user body enters the second chamber.

Preferably, in the above electronic system, the first acquisition apparatus may include a first acquisition sub-apparatus arranged in the first body and configured to acquire a first parameter, and a second acquisition sub-apparatus arranged in the second body and configured to acquire a second parameter;

the triggering data may include the first parameter and the second parameter; and the processing apparatus may be further configured to determine a spatial parameter of the first part of the user body and/or a spatial parameter of the second part of the user body based on the first parameter and the second parameter, and control the electronic system to perform a preset function based on the spatial parameter.

Preferably, in the above electronic system, the first communication apparatus may be further configured to acquire the second parameter and send the second parameter to the processing apparatus; and the processing apparatus may be connected to the first acquisition sub-apparatus to acquire the first parameter.

Preferably, the above electronic system may further include a second communication apparatus configured to acquire the second parameter and send the second parameter to the processing apparatus, where the second communication apparatus may be separate from the first communication apparatus, and the processing apparatus may be connected to the first acquisition sub-apparatus to acquire the first parameter.

The present disclosure further provides a control method, which includes:

acquiring triggering data detected by a first acquisition apparatus;

determining whether the detected triggering data meets a first condition; and controlling an electronic system to perform a preset function based on a result of the determination.

Preferably, in the above control method, the controlling the electronic system to perform the preset function based on the result of the determination may include:

generating a control instruction for controlling the electronic system to switch from a first mode to a second mode in a case that the triggering data meets the first condition.

Preferably, the above control method may further include controlling a second acquisition apparatus to switch from a data acquisition mode to a sleep mode or from a sleep mode to a data acquisition mode in a case that the triggering data meets the first condition.

Preferably, the above control method may further include generating a control instruction for controlling a first electronic device to switch from a first mode to a second mode in a case that the triggering data meets the first condition.

It can be seen from the above description that, the electronic system according to the present disclosure includes: the maintenance apparatus configured to maintain a position of the electronic system relative to the user in a case that the electronic system is worn by the user; the first acquisition apparatus configured to detect triggering data; and the processing apparatus configured to determine whether the triggering data meets the first condition and control the electronic system to perform the preset function based on the result of the determination. When using a wearable electronic device including the electronic system, the user can control the electronic system to perform a preset function only by triggering the first acquisition apparatus, and hence the control operation is simple. And the control method can be used for driving the electronic system to perform a preset function, and hence the operation is simple.

BRIEF DESCRIPTION OF THE DRAWINGS

The drawings to be used in the description of the embodiments or the conventional technology will be described briefly as follows, so that the technical solutions according to the embodiments of the present disclosure or according to the conventional technology will become clearer. It is apparent that the drawings in the following description only illustrate some embodiments of the present disclosure. For those skilled in the art, other drawings may be obtained according to these drawings without any creative work.

DETAILED DESCRIPTION

The technical solutions according to the embodiments of the present disclosure will be described clearly and completely as follows in conjunction with the appended drawings. It is apparent that the described embodiments are only some rather than all of the embodiments according to the present disclosure. Any other embodiments obtained by those skilled in the art based on the embodiments in the present disclosure without any creative work fall within the scope of protection of the present disclosure.

As described in the background, a conventional wearable electronic device needs to be used with a mobile terminal, such as smart running shoes. A user wearing the smart running shoes needs to start a recording function of the smart running shoes via a mobile phone if the user wants to record running data.

As can be seen, it is complex and not convenient for a wearer to use the wearable electronic device in a case that the wearable electronic device is controlled by a mobile terminal to perform a preset function. Some of the functions of the wearable electronic device may be achieved by installing preset software in the mobile terminal. For example, data such as a running distance of the user may be recorded by installing running software in a mobile phone. However, in this case, only some specified functions can be achieved via an existing sensor or acquisition apparatus of the mobile terminal, hence the application field of the wearable electronic device is limited and the user has to carry the mobile terminal. Under a specified use condition such as running, it is not convenient for the user to run while carrying a mobile terminal with running software, as compared with wearing a wearable electronic device directly on a part of a user body.

In order to address the above issue, an electronic system is provided in an embodiment of the present disclosure. The electronic system may be directly worn on a preset part of the user body, and perform a preset function based on detected triggering data without a mobile terminal, thereby simplifying the operation and providing convenience in use.

Figure 1:
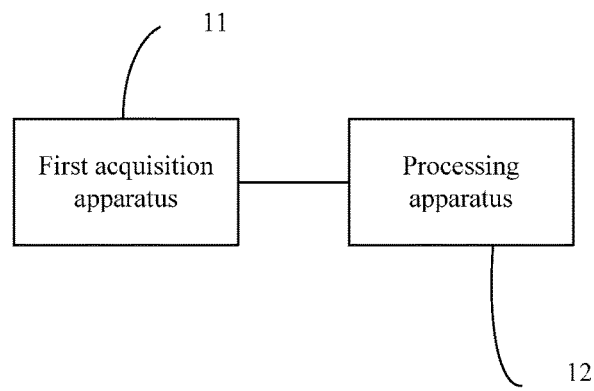
FIG. 1 is a schematic structural diagram of an electronic system according to an embodiment of the present disclosure.

FIG. 1 is a schematic structural diagram of an electronic system according to an embodiment of the present disclosure. The electronic system includes a first acquisition apparatus 11 and a processing apparatus 12. The first acquisition apparatus 11 is communicatively connected to the processing apparatus 12 for data transmission. The first acquisition 11 may be communicatively connected to the processing apparatus 12 in a wireless or/and wired way.

The first acquisition apparatus 11 is configured to detect triggering data. The processing apparatus 12 is configured to determine whether the triggering data meets a first condition and control the electronic system to perform a preset function based on the result of the determination.

The electronic system further includes a maintenance apparatus, for wearing the electronic device including the electronic system. The maintenance apparatus is configured to maintain a position of the electronic system relative to a user in a case that the electronic system is worn by the user. The first acquisition apparatus 11 and the processing apparatus 12 may be arranged on a surface of the maintenance apparatus or embedded into the maintenance apparatus.

In this electronic system, the first acquisition apparatus 11 acquires the triggering data, and the processing apparatus 12 controls the electronic system based on the triggering data without a mobile terminal, thereby simplifying the operation and providing convenience in use.

In the electronic system according to an embodiment of the present disclosure, in a case that the triggering data meets the first condition, the processing apparatus 12 generates a control instruction for controlling the electronic system to switch from a first mode to a second mode.

Optionally, the electronic system may be operable in a display mode and a non-display mode. In a case that the triggering data meets the first condition, the processing apparatus may be configured to generate a control instruction for controlling the electronic system to switch from the display mode to the non-display mode or from the non-display mode to the display mode. In an embodiment, the electronic system may be configured to include a display apparatus which is controlled via the control instruction to switch between the display mode and the non-display mode.

Optionally, the electronic system may be operable in a night mode and a day mode. In a case that the triggering data meets the first condition, the processing apparatus may be configured to generate a control instruction for controlling the electronic system to switch from the night mode to the day mode or from the day mode to the night mode. In an embodiment, the electronic system may be configured to include a light-emitting apparatus which is controlled via the control instruction to switch between the night mode and the day mode.

Figure 2:
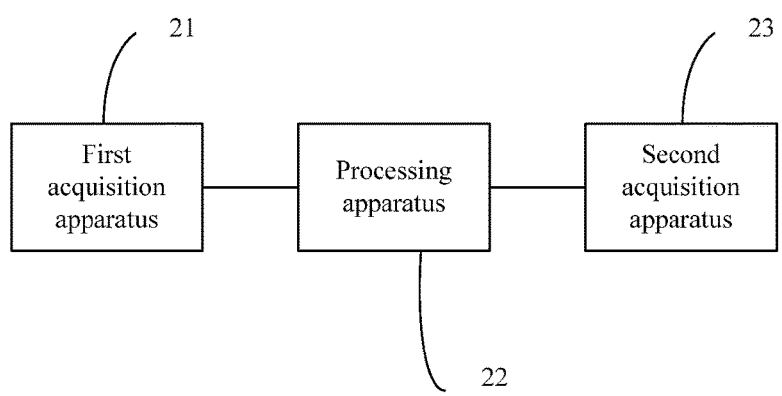
FIG. 2 is a schematic structural diagram of another electronic system according to an embodiment of the present disclosure.

FIG. 2 is a schematic structural diagram of another electronic system according to an embodiment of the present disclosure. The electronic system includes a first acquisition apparatus 21, a processing apparatus 22 and a second acquisition apparatus 23. The first acquisition 21 and the processing apparatus 22 have a same function and a same connection relationship as that in the embodiment shown in FIG. 1 respectively. Based on the embodiment shown in FIG. 1, the embodiment shown in FIG. 2 further includes the second acquisition apparatus 23. The second acquisition apparatus 23 is communicatively connected to the processing apparatus 22 in a wireless and/or wired way for data transmission.

The second acquisition apparatus 23 is operable in a data acquisition mode and a non-data acquisition mode. In a case that the triggering data meets the first condition, the processing apparatus 22 is further configured to control the second acquisition apparatus 23 to switch from the data acquisition mode to the non-data acquisition mode or from the non-data acquisition mode to the data acquisition mode. In an embodiment, whether the triggering data meets the first condition may be determined as follows. The processing apparatus 22 determines whether triggering data detected by the first acquisition apparatus 21 matches with standard data, and the triggering data is determined to meet the first condition in a case of a positive determination.

As can be seen, in the electronic system, switching of the second acquisition apparatus 23 between different operating modes is controlled directly based on the triggering data detected by the first acquisition apparatus 21, thereby simplifying the operation and providing convenience in use.

Figure 3:
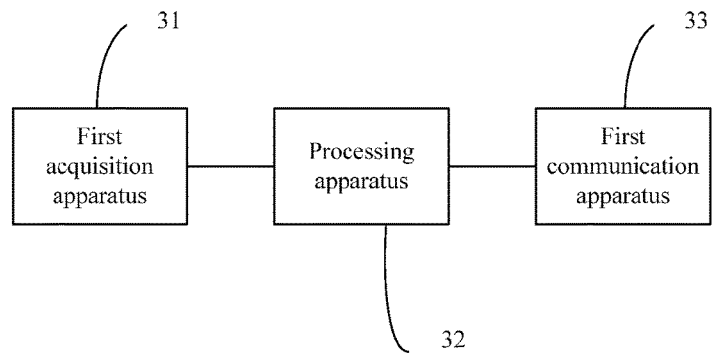
FIG. 3 is a schematic structural diagram of another electronic system according to an embodiment of the present disclosure.

FIG. 3 is a schematic structural diagram of another electronic system according to an embodiment of the present disclosure. The electronic system includes a first acquisition apparatus 31, a processing apparatus 32 and a first communication apparatus 33. The first acquisition 31 and the processing apparatus 32 have a same function and a same connection relationship as that in the embodiment shown in FIG. 1 respectively. Based on the embodiment shown in FIG. 1, the embodiment shown in FIG. 3 further includes the first communication apparatus 33. The first communication apparatus 33 is communicatively connected to the processing apparatus 32 in a wireless and/or wired way for data transmission.

In a case that the triggering data meets the first condition, the processing apparatus 32 is configured to send a control instruction to a first electronic device via the first communication apparatus 33 for controlling the first electronic device to switch from a first mode to a second mode.

As with the above embodiment, in an embodiment, whether the triggering data meets the first condition may be determined as follows. The processing apparatus 32 determines whether triggering data detected by the first acquisition apparatus 31 matches with standard data, and the triggering data is determined to meet the first condition in a case of a positive determination.

The first electronic device may be a mobile terminal device, such as a mobile phone and a tablet computer. In a case that the electronic system is worn by a user, the user may control a mobile terminal device to switch between different modes via the electronic system, instead of controlling the mobile terminal device, hence it is convenient to control the mobile terminal device.

Figure 4:
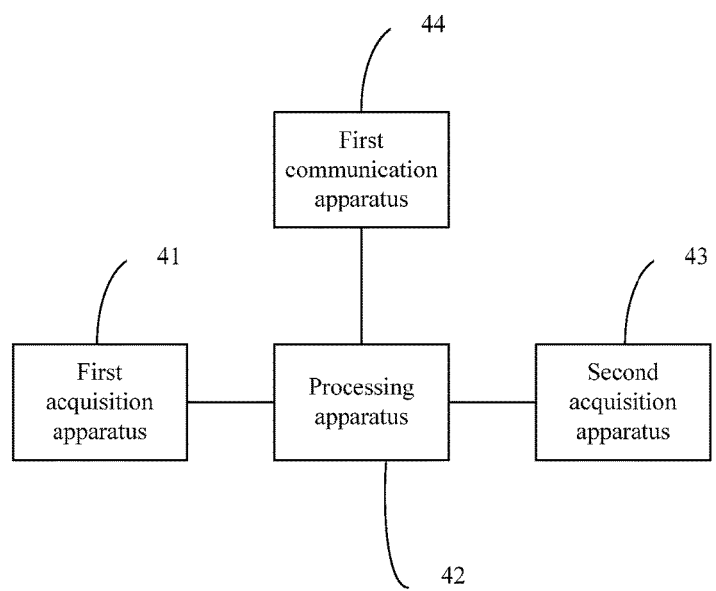
FIG. 4 is a schematic structural diagram of another electronic system according to an embodiment of the present disclosure.

FIG. 4 is a schematic structural diagram of another electronic system according to an embodiment of the present disclosure. The electronic system includes a first acquisition apparatus 41, a processing apparatus 42, a second acquisition apparatus 43 and a first communication apparatus 44. The first acquisition 41 and the processing apparatus 42 have a same function and a same connection relationship as that in the embodiment shown in FIG. 1 respectively. Based on the embodiment shown in FIG. 1, the embodiment shown in FIG. 4 further includes the second acquisition apparatus 43 and the first communication apparatus 44.

The second acquisition apparatus 43 and the first communication apparatus 44 each are communicatively connected to the processing apparatus 42 in a wireless and/or wired way.

In the electronic system shown in FIG. 4, the second acquisition apparatus 43 may also be operable in a data acquisition mode and a non-data acquisition mode. In a case that the triggering data meets the first condition, the processing apparatus 42 is further configured to control the second acquisition apparatus 43 to switch from the data acquisition mode to the non-data acquisition mode or from the non-data acquisition mode to the data acquisition mode.

In a case that the triggering data meets the first condition, the processing apparatus 42 is configured to send a control instruction to a first electronic device via the first communication apparatus 44 for controlling the first electronic device to switch from a first mode to a second mode.

In the embodiment shown in FIG. 4, different pieces of triggering data may correspond to different first conditions. The first condition includes a first condition corresponding to the second acquisition apparatus 43 and a first condition corresponding to the first communication apparatus 44. The processing apparatus 42 control the second acquisition apparatus 43 to switch between different modes based on the first condition corresponding to the second acquisition apparatus 43. And the processing apparatus 42 controls the first communication apparatus 44 to send a control instruction to the first electronic device based on the first condition corresponding to the first communication apparatus 44, for controlling the first electronic device to switch from a first mode to a second mode.

In the embodiment shown in FIG. 4, the processing apparatus 42 controls the second acquisition apparatus 43 and the first communication apparatus 44 respectively based on different first conditions. Therefore, whether the triggering data meets the first condition may be determined as follows. Multiple first conditions are provided. The first conditions include a first condition corresponding to the first communication apparatus 44 and a first condition corresponding to the second acquisition apparatus 43. Each of the first conditions independently corresponds to one piece of standard data. The processing apparatus 42 queries standard data matching with triggering data detected by the first acquisition apparatus 41. If the standard data matching with the triggering data exists, the triggering data meets the first condition corresponding to the standard data; or else, the triggering data does not meet the first condition.

In the electronic system according to the above embodiments, the first acquisition apparatus may be configured to be operable only in a trigger detection mode. In this case, the first acquisition apparatus may only be configured to detect triggering data, and the processing apparatus is configured to determine whether the detected triggering data meets the first condition.

In other embodiments, the first acquisition apparatus may be configured to be operable in a trigger detecting mode and a data recording mode. In a case that the triggering data meets the first condition, the processing apparatus is further configured to control the first acquisition apparatus to switch from the trigger detecting mode to the data recording mode or from the data recording mode to the trigger detecting mode. In this case, the first conditions include a first condition corresponding to a mode switching of the first acquisition apparatus.

In the electronic system according to the embodiment of the present disclosure, the first acquisition apparatus may be a spatial acquisition apparatus for acquiring a spatial posture parameter or a spatial movement parameter. The spatial posture parameter includes but is not limited to a hand posture, a body posture, a foot or log posture and the like, of a user. The movement parameter includes but is not limited to acceleration, a speed, a height and the like. The first acquisition apparatus may also be a pressure sensor for acquiring a pressure parameter. In a case that the electronic system includes a second acquisition apparatus, the second acquisition apparatus may be one or more of a spatial acquisition apparatus, a pressure sensor and a biometric parameter sensing sensor. The biometric parameter sensing sensor includes but is not limited to a sensor for acquiring a pulse parameter and a temperature parameter of the user.

The electronic system according to an embodiment of the present disclosure may only include one body structure. For example, the maintenance apparatus of the electronic system may have a ring-shaped structure or a chain-shaped structure, and other apparatuses of the electronic system may be arranged on a surface of the maintenance apparatus or embedded into the body. Specifically, the electronic system may be a smart bracelet, a smart necklace, smart glasses, a smart watch and the like.

In a case that the electronic system is worn by a user on a specified part of a user body and contacts with the specified part, the first acquisition apparatus of the electronic system may be a pressure sensor. When the electronic system is worn by the user, the triggering data detected by the pressure sensor is a pressure signal. The processing device controls the electronic system to perform a preset function upon detection that the pressure signal meets the first condition.

For example, in a case that the electronic system includes a second acquisition apparatus, it may be defined that: a detected pressure signal meets a first condition in a case that the electronic system is worn by the user and a pressure value is larger than a preset threshold; and the detected pressure signal does not meet the first condition in a case that the electronic system is not worn by the user and the pressure value is zero. The processing apparatus controls the second acquisition apparatus to switch to a data acquisition mode upon detection that the pressure signal meets the first condition. The processing apparatus controls the second acquisition apparatus to switch to a non-data acquisition mode upon detection that the pressure signal does not meet the first condition. In this case, an operating mode of the second acquisition apparatus may be controlled without a specialized control button or a manually-input instruction, thereby simplifying the control operation and providing convenience in use.

An error triggering may occur in a case that only one first acquisition apparatus is adopted to detect a triggering signal. In order to achieve a more accurate control operation and a better usage effect, the electronic system according to the embodiment of the present disclosure may include multiple bodies, and the first acquisition apparatus may be configured to include multiple acquisition sub-apparatuses.

Figure 5:
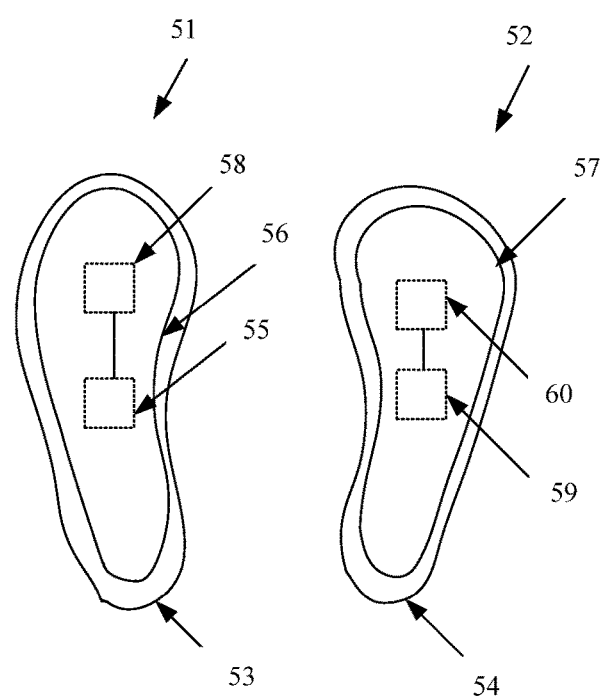
FIG. 5 is schematic structural diagram of another electronic system according to an embodiment of the present disclosure.

FIG. 5 is a schematic structural diagram of another electronic system according to an embodiment of the present disclosure. The electronic system includes a first body 51 and a second body 52. In this case, a maintenance apparatus of the electrode system includes a first maintenance apparatus 53 arranged in the first body for maintaining a position of the first body 51 on a first part of a user body and a second maintenance apparatus 54 arranged in the second body 52 for maintaining a position of the second body 52 on a second part of the user body. A processing apparatus 55 of the electronic system is arranged in the first body.

The first maintenance apparatus 53 includes a first chamber 56 having an opening, and the second maintenance apparatus 54 includes a second chamber 57 having an opening. A position of the first body 51 relative to the user body may be maintained by the first maintenance apparatus once the first part of the user body enters the first chamber 56, and a position of the second body 52 relative to the user body may be maintained by the second maintenance apparatus once the second part of the user body enters the second chamber 57.

A first acquisition apparatus of the electronic system includes a first acquisition sub-apparatus 58 arranged in the first body 51 for acquiring a first parameter, and a second acquisition sub-apparatus 59 arranged in the second body 52 for acquiring a second parameter. In this case, triggering data detected by the first acquisition apparatus includes the first parameter and the second parameter. The processing apparatus 55 is further configured to determine a spatial parameter of the first part of the user body and/or the second part of the user body based on the first parameter and the second parameter, and control the electronic system to perform a preset function based on the spatial parameter.

Preferably, a first communication apparatus 60 of the electronic system may be arranged in the second body 52. In order to communicatively connect the second acquisition sub-apparatus 59 and the processing apparatus 55, the first communication apparatus 60 may be connected to the second acquisition sub-apparatus 59 to acquire the second parameter and send the second parameter to the processing apparatus 55. The first communication apparatus 60 may be communicatively connected to the second acquisition sub-apparatus 59 in a wired way, thereby reducing energy consumption.

The processing apparatus 55 may be connected to the first acquisition sub-apparatus 58 to acquire the first parameter. And the processing apparatus 55 may be communicatively connected to the first acquisition sub-apparatus 58 in a wired way, thereby reducing energy consumption.

In the embodiment shown in FIG. 5, the first communication apparatus 60 needs to perform a long-distance data communication with a first electronic device while performing a short-distance data communication with the processing apparatus 55. Energy consumption required by the first communication apparatus to perform the short-distance data transmission with the first electronic device is high.

To reduce the energy consumption, in other embodiments, a second communication apparatus may be further arranged in the second body. The second communication apparatus is configured to acquire the second parameter and send the second parameter to the processing apparatus. In an embodiment, the first communication apparatus is separate from the second communication apparatuses, and the processing apparatus is connected to the first acquisition sub-apparatus to acquire the first parameter.

An effective communication distance of the first communication apparatus is larger than an effective communication distance of the second communication apparatus. In a case that the second communication apparatus which has the smaller effective communication distance is adopted to transmit data between the second acquisition sub-apparatus and the processing apparatus, the energy consumption is reduced.

The processing apparatus is communicatively connected to the first acquisition sub-apparatus directly in a wired way, and the second communication apparatus is communicatively connected to the second acquisition sub-apparatus in a wired way.

In a case that the first parameter meets a first condition corresponding to the first parameter and the second parameter meets a first condition corresponding to the second parameter, it is determined that the triggering data meets a first condition. Two bodies and two acquisition sub-apparatuses are arranged in the electronic system, thereby avoiding an error triggering and improving the accuracy of control.

Moreover, the triggering data may be diversified by arranging two acquisition sub-apparatuses in different bodies. And more spatial posture parameters or spatial movement parameters of a user may be acquired via the two acquisition sub-apparatuses, for controlling the second acquisition apparatus and/or the first electronic device to perform multiple functions corresponding to multiple first conditions.

In the embodiment shown in FIG. 5, the first body and the second body may be shoes. Different postures of two feet of the user or different separation distances between the two feet of the user may be acquired via the first acquisition sub-apparatus and the second acquisition sub-apparatus.

In a case that the first and second bodies of the electronic system are respectively worn on two feet of the user, the processing apparatus 55 may control the electronic system to perform preset functions based on different postures of the feet of the user and separation distances between the two feet, for achieving local operation control.

For example, the first acquisition sub-apparatus 58 and the second acquisition sub-apparatus 59 are spatial parameter acquisition apparatuses. In a case that the user activates one or two ankles, the processing apparatus 55 may control the first acquisition apparatus to switch from the trigger detecting mode to the data recording mode based on an acceleration of the ankle(s) acquired by a corresponding acquisition sub-apparatus. In this case, the user may start the first acquisition apparatus to acquire running data with a foot action, thereby simplifying the operation and providing convenience in use. Spatial parameter thresholds for the two acquisition sub-apparatuses may be set according to a habit of the user, to specify trigger actions conforming to the exercise habit of the user.

Alternatively, in a case that the user activates one or two ankles, the processing apparatus 55 may be configured to control the second acquisition apparatus to switch from the data acquisition mode to the non-data acquisition mode or from the non-data acquisition mode to the data acquisition mode based on an acceleration parameter of the ankle(s) acquired by a corresponding acquisition sub-apparatus. In this case, the first acquisition apparatus can be triggered only by a foot action, and the processing apparatus 55 controls the second acquisition apparatus to switch between different modes based on the acceleration to the ankle(s) acquired by the corresponding acquisition sub-apparatus, and hence the operation is simplified and quick.

In a case that the first and second bodies of the electronic system are respectively worn on two feet of the user, the processing apparatus 55 may control the first electronic device to perform preset functions based on different postures of the feet of the user and different separation distances between the feet, thereby achieving local operation control. The first electronic device may be a mobile phone.

For example, the first acquisition sub-apparatus 58 may be configured to acquire a spatial orientation of the first body 51 and a distance between the first body 51 and the second body 52. The second acquisition sub-apparatus 59 may be configured to acquire a spatial orientation of the second body 52 and a distance between the second body 52 and the first body 51. And postures of the feet and a distance between the feet may be determined based on the first parameter acquired by the first acquisition sub-apparatus 58 and the second parameter acquired by the second acquisition sub-apparatus 59.

In this case, the processing apparatus 55 may control the first acquisition apparatus and/or the second acquisition apparatus to switch between different modes based on different foot postures and different separation distances between the feet. The processing apparatus 55 may control the mobile phone to perform preset functions based on different foot postures and different separation distances between the feet. For example, the processing apparatus may control the mobile phone to start a music player, in a case of determining based on the first and second parameters that a distance between the first body 51 and the second body 52 is the same as the width of a shoulder; and may control the mobile phone to start a text information editing function, in a case of determining based on the first and second parameters that the first body 51 and the second body 52 form a T shape. Different functions of the mobile phone may be started in a way of corresponding thresholds of the first and second parameters to different foot positions, instead of finding applications corresponding to respective functions on the mobile phone, thereby simplifying the operation and providing convenience in use.

The processing apparatus 55 determines a separation distance between a back end of the first body 51 and a back end of the second body 52 and a separation distance between a front end of the first body 51 and a front end of the second body 52 based on the first parameter and the second parameter, and then determines whether the distance between the two feet is the same as the width of the shoulder or the two feet form a '八' shape. If the separation distance between the back end of the first body 51 and the back end of the second body 52 equals to the separation distance between the front end of the first body 51 and the front end of the second body 52 and equals to the width of the shoulder, it is determined that the distance between the first body 51 and the second body 52 is the same as the width of the shoulder. If separation distance between the back end of the first body 51 and the back end of the second body 52 is less than the separation distance between the front end of the first body 51 and the front end of the second body 52, it is determined that the first body 51 and the second body 52 form a '八' shape.

The processing apparatus 55 determines an orientation of the first body 51 and an orientation of the second body 52 based on the first parameter and the second parameter and determines whether the first body 51 and the second body 52 form a T shape based on a distance between a front end or back end of one of the two bodies and a middle end of the other of the bodies. In a case that the first body 51 is perpendicular to the second body 52 and a distance between the front end of the first body 51 and the middle end of the second body 52 is zero, it is determined that the first body 51 and the second body 52 form a T shape. The processing apparatus 55 may control the first electronic device to perform different functions based on different postures of the first body 51 and the second body 52.

The first acquisition sub-apparatus 58 may be arranged near or at the opening of the first chamber 56, and the second acquisition sub-apparatus 59 may be arranged near or at the opening of the second chamber 57. In a case that the user rotates with his/her tiptop on the ground, the processing apparatus 55 may determine that an ankle rotates based on a constant gravity acceleration and a horizontal rotation acceleration of the tiptop which are acquired by a corresponding acquisition sub-apparatus, and thus control the electronic system or the first electronic device to perform a preset function.

A light-emitting apparatus may be arranged on an external surface of the first chamber and/or an external surface of the second chamber. The light emitting apparatus is configured to indicate the location of the user or illuminate in a dark environment. And the processing apparatus is further configured to turn on or turn off the light-emitting apparatus in response to the triggering data.

The first acquisition sub-apparatus may be a first gravity acceleration acquisition apparatus arranged on the first body, and the second acquisition sub-apparatus may be a second gravity acceleration acquisition apparatus arranged on the second body. The user wearing the electronic system may start the light-emitting apparatus by stamping his/her feet continuously. Specifically, the processing apparatus may turn on or turn off the light-emitting apparatus in a case that a change frequency of a gravity acceleration acquired by the first acquisition sub-apparatus and a change frequency of a gravity acceleration acquired by the second acquisition sub-apparatus each meet a preset threshold.

Alternatively, the first acquisition sub-apparatus may be a first pressure sensor arranged in the first body and the second acquisition sub-apparatus may be a second pressure sensor arranged in the second body. The user wearing the electronic system may start the light-emitting apparatus by stamping his/her feet continuously. Specifically, the processing apparatus may turn on or turn off the light-emitting apparatus in a case that a pressure value acquired by the first acquisition sub-apparatus and a pressure value acquired by the second acquisition sub-apparatus each meet a preset threshold.

In a case that the electronic system is worn by the user, the processing apparatus determines whether postures of the feet of the user meet a preset first condition and control the second acquisition apparatus or first electronic device to switch between different modes based on the result of the determination. Specifically, if the first electronic device controlled by the electronic system is a mobile phone, the user wearing the electronic system may control the mobile phone to switch between different modes only with a body posture.

As can be seen, the electronic system may control the second acquisition apparatus or first electronic device to switch between different modes with different posture parameters, thereby simplifying the operation and providing convenience in use.

In the electronic system according to the embodiment of the present disclosure, the processing apparatus stores data acquired by the first acquisition apparatus and/or second acquisition apparatus. The processing apparatus sends the data to a terminal device via the first communication apparatus. After being applied independently, the electronic system may share data with the terminal device via the first communication apparatus.

Figure 6:
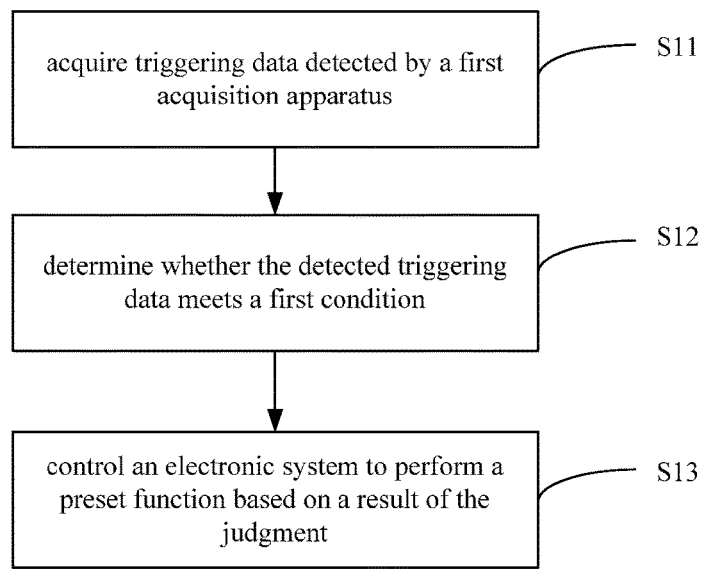
FIG. 6 is a schematic flowchart of a control method according to an embodiment of the present disclosure.

Accordingly to the above electronic system, an embodiment of the present disclosure further provides a control method for the above electronic system provided in the above embodiment, as shown in FIG. 6, which is a schematic flowchart of a control method according to an embodiment of the present disclosure. The control method includes:

Step S11: acquiring triggering data detected by a first acquisition apparatus;

Step S12: determining whether the detected triggering data meets a first condition; and Step S13: controlling an electronic system to perform a preset function based on a result of the determination.

In the control method, the controlling the electronic system to perform the preset function based on the result of the determination may include generating a control instruction for controlling the electronic system to switch from a first mode to a second mode in a case that the triggering data meets the first condition.

Optionally, the control method may further include controlling the second acquisition apparatus to switch from a data acquisition mode to a sleep mode or from a sleep mode to a data acquisition mode in a case that the triggering data meets the first condition. In this case, the electronic system may acquire data independently with the second acquisition apparatus, instead of being used with a mobile terminal.

Optionally, the control method may further include generating a control instruction for controlling a first electronic device to switch from a first mode to a second mode in a case that the triggering data meets the first condition.

With the control method, an electronic system may be controlled to perform a preset function without a mobile terminal, and the first electronic device may be controlled to switch between different modes, thereby simplifying the operation and providing convenience in use.

It should be noted that, the control method is based on the above embodiment of electronic system, and hence the same or similar parts between the method and the above embodiments can be described or supplemented with one another.

With the above descriptions of the disclosed embodiments, the skilled in the art may practice or use the present disclosure. Various modifications to the embodiments are apparent for the skilled in the art. The general principle suggested herein can be implemented in other embodiments without departing from the spirit or scope of the disclosure. Therefore, the present disclosure should not be limited to the embodiments disclosed herein, but has the widest scope that is conformity with the principle and the novel features disclosed herein.

The invention claimed is:

1. An electronic system, comprising:
a fixing structure configured to fix a position of the electronic system relative to a user in a case that the electronic system is worn by the user;
a first sensor configured to detect triggering data; and
a processor configured to determine whether the triggering data meets a first condition, and control the electronic system to perform a preset function based on a result of the determination,
wherein the electronic system comprises a first body and a second body, the fixing structure comprises a first fixing structure arranged in the first body and configured to fix a position of the first body on a first part of a user body, and a second fixing structure arranged in the second body and configured to fix a position of the second body on a second part of the user body, and the processor is arranged in the first body,
wherein the first fixing structure comprises a first chamber having an opening, and the second fixing structure comprises a second chamber having an opening,
wherein a position of the first body relative to the user body is fixed by the first fixing structure once the first part of the user body enters the first chamber, and a position of the second body relative to the user body is fixed by the second fixing structure once the second part of the user body enters the second chamber,
wherein the first sensor comprises a first sub-sensor arranged in the first body and configured to acquire a first parameter, and a second sub-sensor arranged in the second body and configured to acquire a second parameter,
wherein the triggering data comprises the first parameter and the second parameter, and
wherein the processor is further configured to determine a spatial parameter of the first part of the user body and/or a spatial parameter of the second part of the user body based on the first parameter and the second parameter, and control the electronic system to perform a preset function based on the spatial parameter.

2. An electronic system, comprising:
a fixing structure configured to fix a position of the electronic system relative to a user in a case that the electronic system is worn by the user;
a first sensor configured to detect triggering data; and
a processor configured to determine whether the triggering data meets a first condition, and control the electronic system to perform a preset function based on a result of the determination;
wherein the electronic system comprising a first body and a second body, the fixing structure comprises a first fixing structure arranged in the first body and configured to fix a position of the first body on a first part of a user body, and a second fixing structure arranged in the second body and configured to fix a position of the second body on a second part of the user body, and the processor is arranged in the first body,
wherein the first sensor comprises a first sub-sensor arranged in the first body and configured to acquire a first parameter, and a second sub-sensor arranged in the second body and configured to acquire a second parameter,
wherein the triggering data comprises the first parameter and the second parameter; and
wherein the processor is further configured to determine a spatial parameter of the first part of the user body and/or a spatial parameter of the second part of the user body based on the first parameter and the second parameter, and control the electronic system to perform a preset function based on the spatial parameter.

3. The electronic system according to claim 2, further comprising a first transceiver, wherein the first transceiver is configured to acquire the second parameter and send the second parameter to the processor; and
the processor is connected to the first sub-sensor to acquire the first parameter.

4. The electronic system according to claim 3, further comprising a second transceiver configured to acquire the second parameter and send the second parameter to the processor,
wherein the second transceiver is separate from the first transceiver.

5. The electronic system according to claim 4, wherein an effective communication distance of the first transceiver is larger than an effective communication distance of the second transceiver.

* * * * *